United States Patent [19]

Hansen

[11] Patent Number: 5,569,170
[45] Date of Patent: Oct. 29, 1996

[54] PULSATOR

[75] Inventor: Craig N. Hansen, Minnetonka, Minn.

[73] Assignee: Electromed, Inc., Minnetonka, Minn.

[21] Appl. No.: 471,620

[22] Filed: Jun. 5, 1995

Related U.S. Application Data

[63] Continuation-in-part of Ser. No. 90,234, Jul. 12, 1993, Pat. No. 5,453,081.

[51] Int. Cl.[6] .................................................. A61H 9/00
[52] U.S. Cl. .......................... 601/150; 601/149; 601/151; 601/48
[58] Field of Search ................................ 602/13; 601/41, 601/43, 44, 48, 49, 55, 56, 77, 148, 149, 150, 151, 152, 1, 6, 9, 11, 12, 16, 46, 61, 107; 128/DIG. 20; 5/453, 915

[56] References Cited

U.S. PATENT DOCUMENTS

| | | |
|---|---|---|
| 1,898,652 | 2/1933 | Williams . |
| 2,079,694 | 5/1937 | Lovell et al. . |
| 2,354,397 | 7/1944 | Miller . |
| 2,588,192 | 3/1952 | Akerman et al. . |
| 2,780,222 | 2/1957 | Polzin et al. . |
| 2,869,537 | 1/1959 | Chu . |
| 3,043,292 | 7/1962 | Mendelson . |
| 3,310,050 | 3/1967 | Goldfarb . |
| 3,556,088 | 1/1971 | Leonardini . |
| 3,672,354 | 6/1972 | Weber . |
| 3,880,152 | 4/1975 | Nohmura . |
| 3,993,053 | 11/1976 | Grossan . |
| 4,023,566 | 5/1977 | Martinmaas . |
| 4,066,072 | 1/1978 | Cummins . |
| 4,093,944 | 6/1978 | Muncheryan . |
| 4,133,305 | 1/1979 | Steuer . |
| 4,155,356 | 5/1979 | Venegas . |
| 4,232,661 | 11/1980 | Christensen . |
| 4,507,816 | 4/1985 | Smith, Jr. . |
| 4,590,925 | 5/1986 | Dillon . |
| 4,779,615 | 10/1988 | Frazier . |
| 4,805,612 | 2/1989 | Jensen . |
| 4,813,403 | 3/1989 | Endo ........................................ 601/46 |
| 4,838,263 | 6/1989 | Warwick et al. . |
| 4,840,167 | 5/1989 | Olsson et al. . |
| 4,908,895 | 3/1990 | Walker . |
| 4,977,889 | 12/1990 | Budd . |
| 5,020,516 | 6/1991 | Biondi et al. . |
| 5,056,505 | 10/1991 | Warwick et al. . |
| 5,097,821 | 3/1992 | Eakin . |
| 5,113,852 | 5/1992 | Murtonen . |
| 5,233,974 | 8/1993 | Senoue et al. . |
| 5,235,967 | 8/1993 | Arbisi et al. . |

FOREIGN PATENT DOCUMENTS

| | | |
|---|---|---|
| 26799 | 4/1981 | European Pat. Off. . |
| 0173499 | 7/1988 | Japan . |
| 0151396 | 6/1989 | Japan . |
| 0101895 | 4/1990 | Japan . |

Primary Examiner—Richard J. Apley
Assistant Examiner—Jeanne M. Clark

[57] ABSTRACT

An apparatus for generating air pressure pulses delivered to a vest accommodating a person. A diaphragm located within the housing is connected to a wave generator and amplifier operable to vibrate the diaphragm. The vibrating diaphragm produces air pressure pulses which are delivered to the air accommodating receiver to subject the person to repetitive force pulses.

32 Claims, 6 Drawing Sheets

PULSATOR

This is a continuation-in-part of U.S. application Ser. No. 08/090,234, filed Jul. 12, 1993, now U.S. Pat. No. 5,453,081.

FIELD OF THE INVENTION

The invention is directed to a medical device used to apply repetitive compression forces to the body of a person to aid blood circulation, loosening and elimination of mucus from the lungs of a person and relieve muscular and nerve tensions.

BACKGROUND OF THE INVENTION

Artificial respiration devices for applying and relieving pressure on the chest of a person have been used to assist in lung breathing functions, and loosening and eliminating mucus from the lungs. Subjecting the person's chest and lungs to pressure pulses or vibrations decreases the viscosity of lung and air passage mucus, thereby enhancing fluid mobility and removal from the lungs. These devices use vests having air accommodating bladders that surround the chests of persons. Mechanical mechanisms, such as solenoid or motor-operated air valves, supply air under pressure to the bladders in regular patterns of pulses. J. D. Ackerman et al in U.S. Pat. No. 2,588,192, discloses an artificial respiration apparatus having a chest vest supplied with air under pressure with an air pump. Solenoid-operated valves control the flow of air into and out of the vest in a controlled manner to pulsate the vest, thereby subjecting the person's chest to repeated pressure pulses. W. J. Warwick and L. G. Hansen, in U.S. Pat. No. 5,056,505, disclose a chest compression apparatus having a chest vest surrounding a person's chest. A motor-driven rotary valve allows air to flow into the vest and vent air therefrom to apply pressurized pulses to the person's chest.

R. S. Dillion in U.S. Pat. No. 4,590,925 uses an inflatable enclosure to cover a portion of a person's extremity, such as an arm or leg. The enclosure is connected to a fluid control and pulse monitor operable to selectively apply and remove pressure on the person's extremity. R. L. Weber in U.S. Pat. No. 3,672,354 discloses a rest inducing device having an air mattress supplied with air in pulses from an air pump at the frequency of the person's heartbeat.

SUMMARY OF THE INVENTION

The invention is directed to an apparatus for applying pressure pulses to a portion of a person to assist body functions including blood flow, muscle and nerve relaxation and loosening and eliminating mucus from the lungs. The apparatus operates with air under pressure at a selected frequency and force to apply repetitive pressure pulses to a person. In use, the apparatus has a relatively low noise output and can be under the control of the user as well as an attendant.

The apparatus generates repetitive air pressure pulses which are delivered to a receiver, such as a vest, jacket or mattress adapted to accommodate a portion of the body of a person to apply pressure pulses to said person. A housing having an enclosed chamber accommodates a diaphragm which divides the chamber into two separate portions. Air under pressure is supplied with a pump to the chamber to pressurize the apparatus, as well as the receiver. A coil connected to the diaphragm is operable to vibrate the diaphragm to pulsate the air in the chamber. A wave generator generates a wave signal which energizes the coil. An amplifier is used to amplify or provide a gain signal to the coil to control the output of the coil. The wave generator has controls to adjust the frequency of the wave signal as well as the wave form to provide the apparatus with versatility of the type pressure pulse that is applied to the person.

In one embodiment of the apparatus, repetitive pressure pulses are applied to a portion of a person with the use of flexible air accommodating structure that engages a portion of the person to be subjected to repetitive pressure pulses. A pulsator operates to produce air pressure pulses. A hose connects the pulsator with the air accommodating structure so that the air pressure pulses repetitively move the air accommodating structure to apply pressure pulses to a portion of the person. The pulsator has a housing, including an enclosed chamber, which accommodates a diaphragm. The diaphragm divides the chamber into two portions. Air is supplied with a pump to the chamber for subjecting the chamber as well as the flexible air accommodating structure with air under pressure. A coil operates to vibrate the diaphragm to pulsate the air in the chamber. The hose being connected to the housing is open to the chamber so that the air in the air accommodating structure is pulsed, which in turn subjects a portion of the person to repetitive pressure pulses. A wave generator operates to produce a wave signal which drives the coil thereby vibrating the diaphragm to pulsate the air in the chamber and air accommodating structure. An amplifier connected to the wave generator operates to amplify the wave signal to control the output of the coil thereby controlling the vibration intensity of the diaphragm. The amplifier includes a control that is used to adjust the gain of the output signal of the amplifier thereby adjusting the output power of the coil and intensity of the vibrations of the diaphragm. The intensity of the vibrations of the diaphragm alter the air pressure differential of the air in the chamber and air accommodating structure thereby controlling the force of the pressure pulses that are subjected to the person.

In a second embodiment of the apparatus, repetitive pressure pulses are applied to first and second portions of a person in an alternating manner. A pulsator operates to produce air pressure pulses. A first hose connects the pulsator with a first flexible air-accommodating structure that engages the first portion of the person so that air pressure pulses produced by the pulsator repetitively move the first air-accommodating structure to apply pressure pulses to the first portion of the person. A second hose connects the pulsator with a second flexible air-accommodating structure engaging the second portion of the person so that air pressure pulses produced by the pulsator repetitively move the second air accommodating structure unsynchronized with the repetitive movement of the first air-accommodating structure to apply pressure pulses to the second portion of the person at different intervals from the application of pressure pulses to the first portion of the person. The pulsator has a housing, including an enclosed chamber, which accommodates a diaphragm. The diaphragm divides the chamber into two portions. Air is supplied with a pump to each portion of the chamber for subjecting each portion of the chamber as well as the first and second flexible air-accommodating structures with air under pressure. A coil operates to vibrate the diaphragm to pulsate air alternately in each portion of the chamber. The first hose is connected to the housing and is open to one of the chamber portions. The second hose is connected to the housing and is open to the opposite chamber portion. When the diaphragm vibrates, air in the first and second air-accommodating structures is pulsated alternately, which in turn subjects the first and second portions of the person to repetitive pressure pulses in an alternating manner. A wave generator operates to produce a wave signal which drives the coil thereby vibrating the diaphragm to pulsate air in the chamber portions and air-accommodating structures. An amplifier connected to the wave generator is used to amplify the wave signal to control the output of the coil and vibration intensity of the diaphragm. The intensity of the vibrations of the diaphragm alter the air pressure differential of air in each portion of the chamber and each air-accommodating structure thereby controlling the force of the pressure pulses that are subjected to the person.

DESCRIPTION OF PREFERRED EMBODIMENTS

Figure 1:
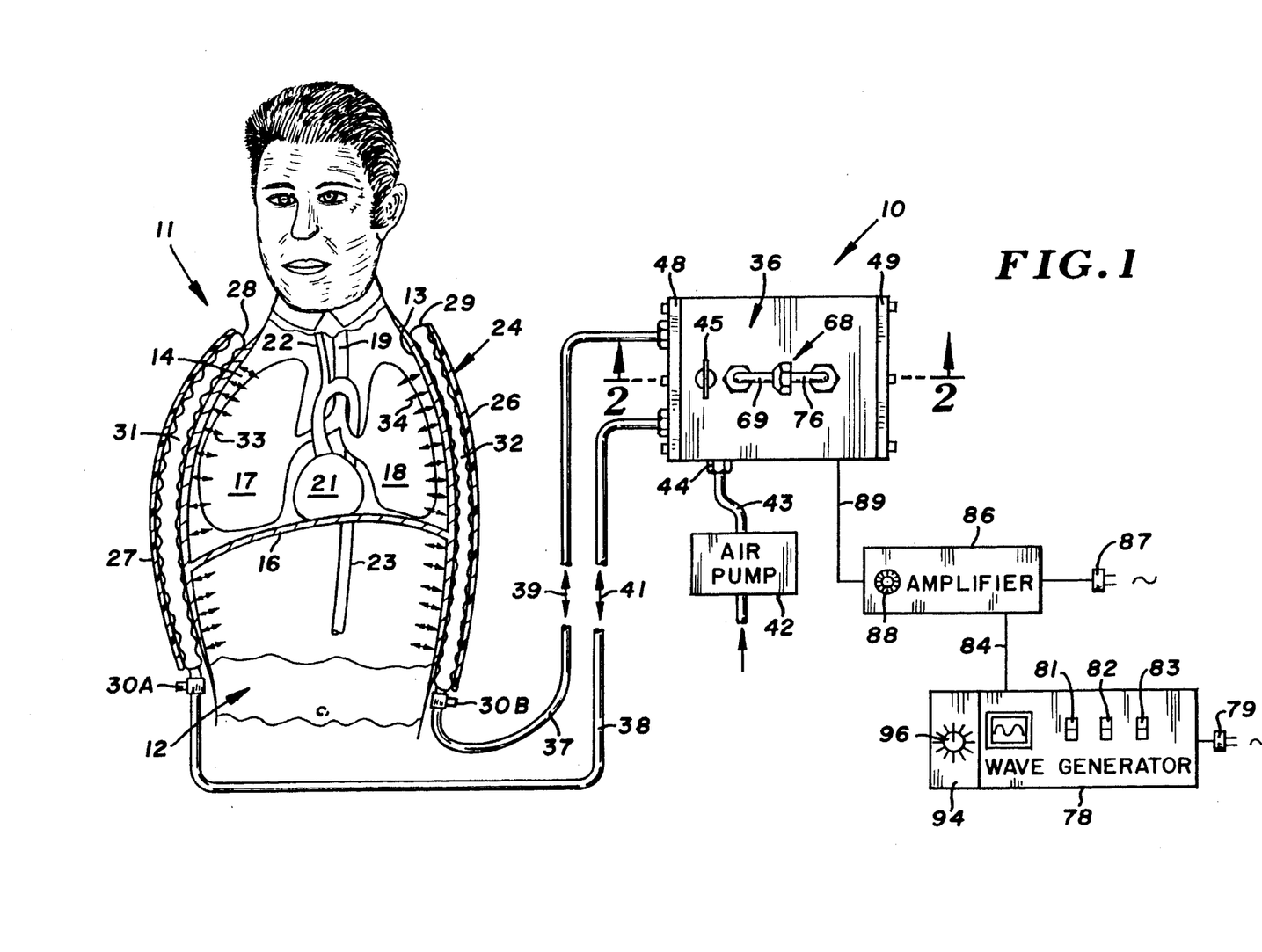
FIG. 1 is a diagrammatic view of the medical device of the invention for applying repetitive force pulses to the body of a human.

Referring to FIG. 1, there is shown a medical device or pulsator, indicated generally at 10, useable to provide repetitive pressure or force pulses to the body of a human to alleviate mucus and fluids in the lungs, to aid in blood circulation and relieve muscular tensions. Person 11 has a body 12 including thorax wall 13 surrounding a chest cavity 14. The lower part of chest cavity 14 has transverse diaphragm 16 located below lungs 17 and 18. Trachea 19 leads from lungs 17 and 18 to the mouth of the person. Chest cavity 14 also accommodates the heart 21, which pumps blood under pressure through systematic aorta 22 and descending artery 23.

A vest, indicated generally at 24, is positioned about body 12. Vest 24 comprises outer jackets 26 and 27 placed about the front and back of thorax wall 13. Jackets 26 and 27 surround flexible air bags or cores 28 and 29 having internal chambers 31 and 32. The material of air bags 28 and 29 is flexible, with the inner side of each air bag located adjacent thorax wall 13. Jackets 26 and 27 are made of rigid shells or non-elastic material that has sufficient rigidity to direct the pulsating forces indicated by arrows 33 and 34, caused by changes of air pressure in air bags 28 and 29 to be directed inwardly into the body toward lungs 17 and 18. Body 12 has reaction forces to the pressure pulses which further enhance the advantageous functions of the device. Medical device 10 can be connected to and adapted to fit around a human leg, thigh or arm to apply repetitive forces to the leg, thigh or arm. An example of the repetitive forces that aids in blood circulation and massages is disclosed by R. S. Dillion in U.S. Pat. No. 4,590,925.

Figure 2:
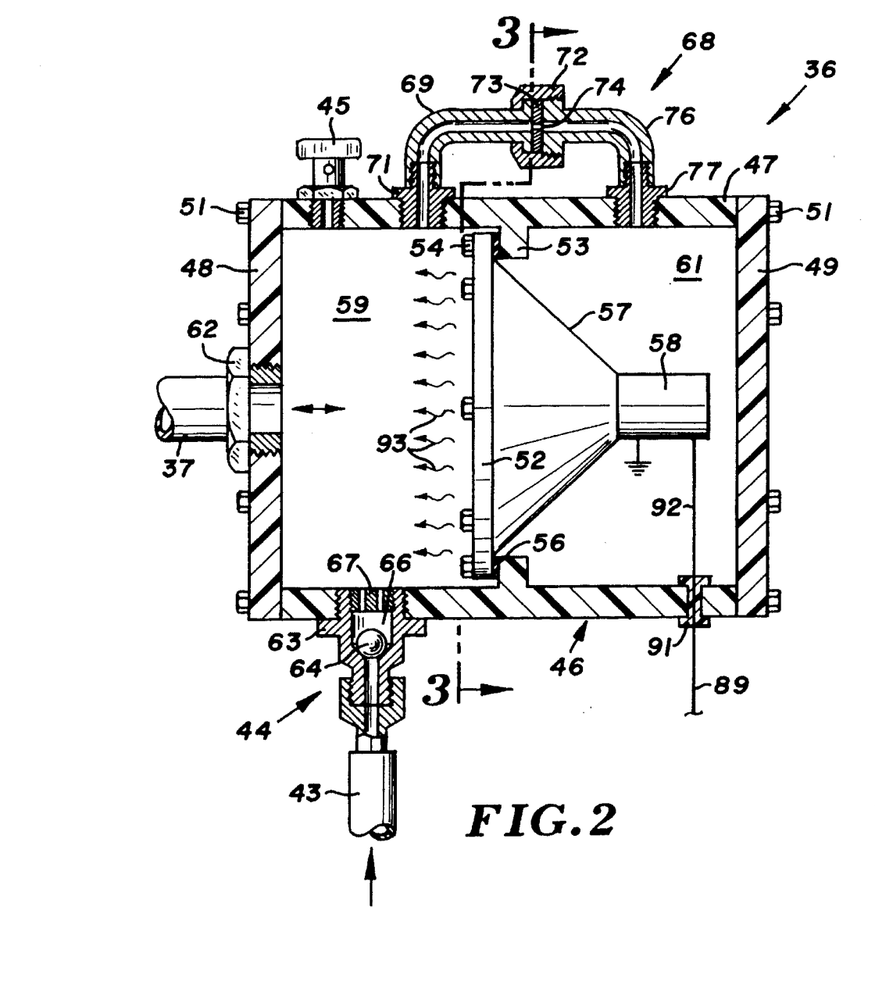
FIG. 2 is an enlarged sectional view taken along the line 2—2 of FIG. 1.

Air bags 28 and 29 are connected to a pulsator, indicated generally at 36, with air lines or hoses 37 and 38. Hoses 37 and 38 are tubular members of flexible non-electrical conductive material so that the body of the person is not subjected to electrical energy from pulsator 36, amplifier 86 or wave generator 78. Hoses 37 and 38 carry pulses of air under pressure indicated by arrows 39 and 41 to chambers 31 and 32 of air bags 28 and 29. Pulsator 36 is connected to air pump 42 with hose 43. Air pump 42 operates to initially pressurize the air in pulsator 36, lines 37 and 38 and chambers 31 and 32 to a selected pressure, such as 1 psi. Air pressure relief valves 30A and 30B connected to lines 37 and 38 and air bags 28 and 29, prevent air flow out and adverse pressure on body 12. An example of an air pressure relief valve is disclosed in U.S. Pat. No. 4,908,895. As seen in FIG. 2, line 43 is connected to check valve 44 operable to allow air into pulsator 36 and prevent the escape of air from pulsator 36 and air bags 28 and 29.

Figure 3:
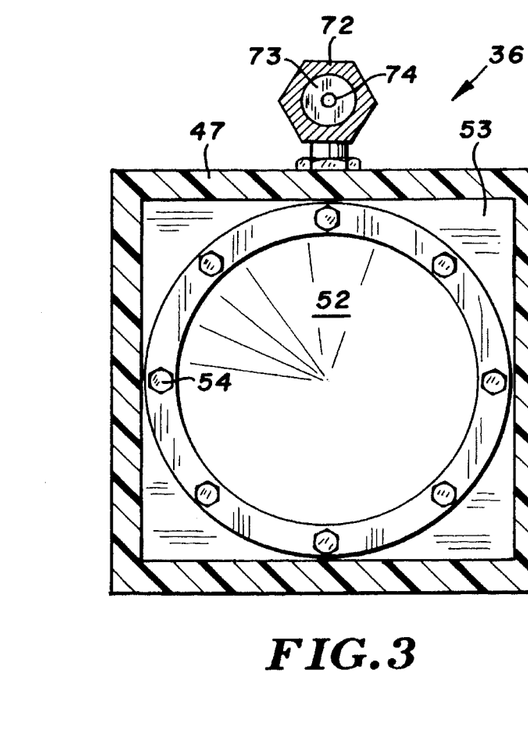
FIG. 3 is a sectional view taken along the line 3—3 of FIG. 2.

Pulsator 36, as seen in FIGS. 2 and 3, has housing 46 comprising side wall 47 connected to end walls 48 and 49 with bolts 51. Diaphragm 52 bisects the mid-portion of housing 46. The outer edge portion of diaphragm 52 is mounted on an inwardly directed rib 53 with a plurality of bolts 54. Cushion or vibration insulation material 56 is interposed between diaphragm 52 and rib 53. Diaphragm 52 is connected to conical shell 57 supporting an electric coil 58 operable to vibrate diaphragm 52. Diaphragm 52 bisects the internal space of housing 46 into first chamber 59 and second chamber 61.

Hose 37 is secured to end wall 48 with tubular connector 62, which allows the air in chamber 59 to flow through hose 37 to air chamber 32 of air bag 29. A second hose 38 is also connected to end wall 48 and carries air under pressure to chamber 31 of air bag 28. A single tube or hose can be used to connect air bags 28 and 29 with pulsator 36.

Returning to FIG. 2, check valve 44 has connector or housing 63 having chamber 66 accommodating check ball 64. The inner end of chamber 66 is closed with perforated plug 67 to allow air to flow through the check valve into chamber 59. Ball 64, when lowered on its seat, blocks the reverse flow of air from chamber 59 back into hose 43 leading to pump 42. Other types of check valves can be used to maintain the air pressure within pulsator 36 and air bags 28 and 29. A manually operated open and closed valve 45 mounted on wall 47 is used to vent air from chamber 59 and relieve the air pressure from air bags 28 and 29. Hoses 37 and 38 can also be uncoupled from end wall 48 to allow air to escape to the atmosphere.

Pulsator 36 has an air pressure balance device, indicated generally at 68, to balance the air pressure between chambers 59 and 61. Device 68 has a first elbow or tube 69 connected to a nipple connector 71, mounted on side wall 47 and open to chamber 59. Elbow 69 has female end 72 that accommodates disk 73 having a small central hole 74 that restricts the flow of air between chambers 59 and 61. Second elbow 76, joined to nipple connector 77, mounted on side wall 47, is open to chamber 61. Elbow 76 is connected to female end 72 and thereby provides a continuous restricted passage for air between chambers 59 and 61.

Returning to FIG. 1, pulsator 36 is driven with wave generator 78 connected to an AC electrical power source with plug 79. Wave generator 78 has a plurality of switches 81, 82 and 83, operable to select a desired wave form, such as a square wave, a sinusoidal wave, or a spike wave, as well as other wave forms. Generator 78 has a wave frequency control 94 having adjusting dial 96. Operator or person 11 can manually use dial 96 to adjust the frequency of the signal sent to amplifier 86. The operator or patient can select the wave form and frequency of the signal with generator 78. Amplifier 86 is used to control the power of the signal sent to coil 58 thereby controlling the vibrations and air pumping characteristics of diaphragm 52. Line 84 connects wave generator 78 to amplifier 86, powered by an electrical power source, such as AC power. Other electric power sources can be used to operate wave generator 78 and amplifier 86. Wave generator 78 and amplifier 86 can be located within a casing that includes pulsator 36. Amplifier 86 has a control 88 operable to adjust the amplification or gain of a power signal carried by line 89 to coil 58, thereby controlling the output power of coil 58 and amplitude of the vibrations of diaphragm 52. The vibrations of diaphragm 52 cause air pressure changes or flexion of pressure pulses which are transmitted by the air in the system to air bags 28 and 29. The frequency of the power signal is determined by the operation of frequency control 94. Line 89 is plugged into electrical connector 91 that is connected with line 92 to coil 58. Vibrating diaphragm 52 generates air pressure differences or force pulses indicated by arrows 93 in FIG. 2 in the air in chamber 59. These pulses are a ripple pressure wave which increase and decrease the pressure of the air in chamber 59 and air cores 28 and 29 in an air pressure change range of 0.25 psi. Other differences in air pressure can be generated by pulsator 36.

In use, vest 24 is placed about body 12 of human 11 and covers the torso from the thoracic wall 13 around lungs 17 and 18. Air pump 42 is operated to inflate air bags 28 and 29 to a selected pressure, such as 1 psi. Air pressure relief valves 30A and 30B are useable to prevent excessive air pressure in air bags 28 and 29. When the selected pressure is obtained, air pump 42 is turned OFF, as check valve 44 maintains the air pressure in air bags 28 and 29, as well as pulsator 36. Wave generator 78 establishes the wave signal, which is amplified by amplifier 86 to drive coil 58. Operation of coil 58 causes diaphragm 52 to vibrate thereby establishing the ripple pressure wave in air chamber 59. The result is that air bags 28 and 29 transmit controlled air pressure pulses as indicated by arrows 33 and 34 to thoracic wall 13 to facilitate the loosening and elimination of mucus from the lungs of a person, aid blood circulation and relieve muscular and nerve tensions. Valve 45 is opened to vent air from the system which deflates air bags 28 and 29. Vest 24 can then be removed from body 12.

Figure 4:
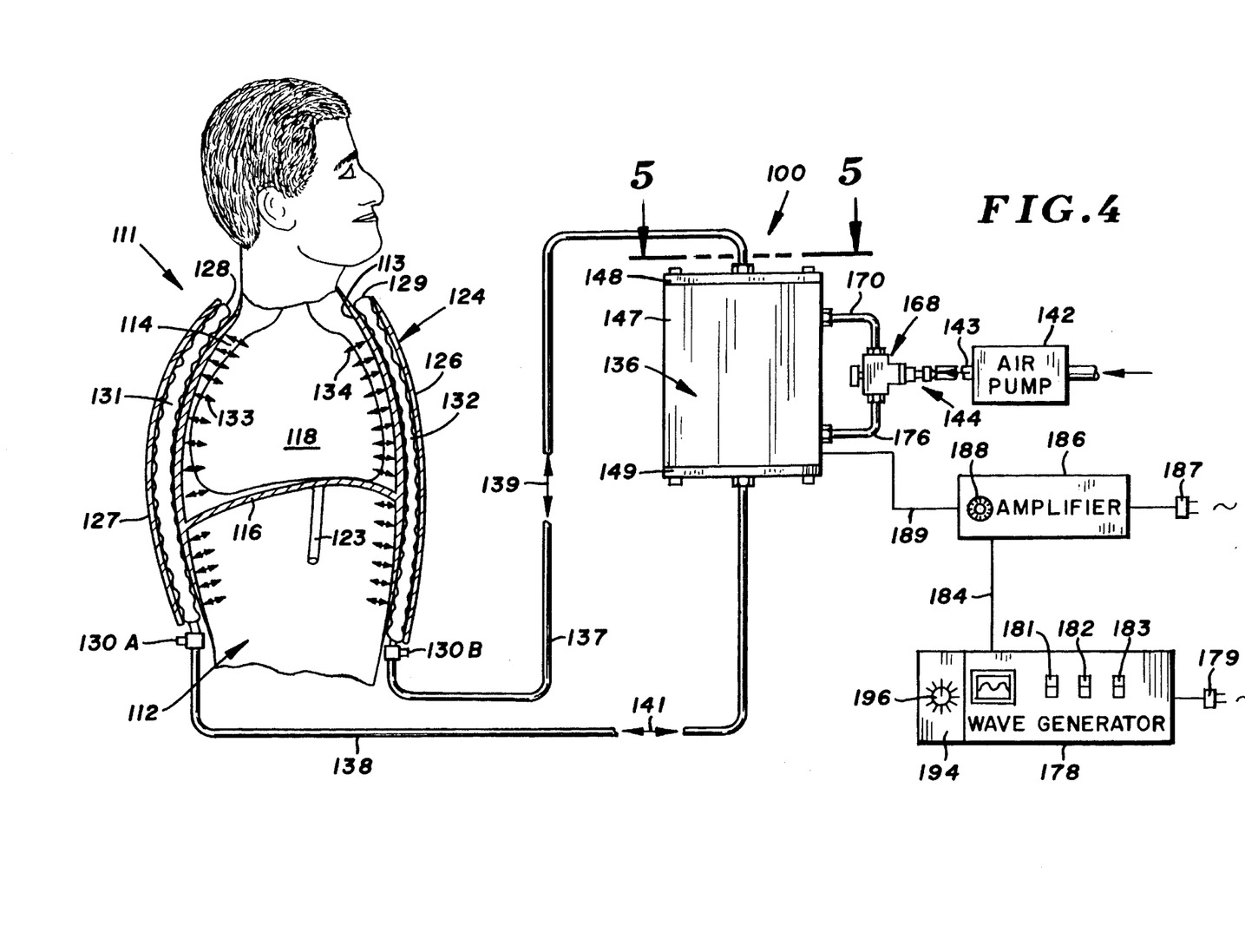
FIG. 4 is a diagrammatic view of a modification of the medical device of the invention for applying repetitive force pulses to the body of a human.

Referring to FIG. 4, there is shown a diagrammatic illustration of a modification of the medical device useable to provide repetitive pressure or force pulses to the body of a human, indicated generally at 100. Medical device 100 is used to subject persons to repetitive force pulses to alleviate muscle and nerve tensions and facilitate blood circulation. Person 111 has a body 112 including a thorax wall 113 surrounding a chest cavity 114. The lower part of chest cavity 114 has transverse diaphragm 116 located below lung 118. Chest cavity 114 also accommodates descending artery 123. Medical device 100 has the same operating structure as the medical device shown in FIGS. 1–3. The corresponding parts have the same reference numbers with the prefix "1". Pulsator 136 is electrically coupled to amplifier 186, which receives a signal from wave generator 178. Wave generator 178 has a wave frequency adjusting control 194 for controlling the frequency of the output signal that is supplied to amplifier 186. The frequency of the pulses, as well as the amplitude of the pulses, is individually controlled to allow pulsator 136 to deliver controlled pulsating air pressure forces to vest 124.

Vest 124 is positioned about body 112. Vest 124 comprises outer jackets 126 and 127 placed about the front and back of thorax wall 113. Jackets 126 and 127 surround air bags 128 and 129 having internal chambers 131 and 132. Air bags 128 and 129 are separately sealed from each other. The material of air bags 128 and 129 is flexible with the inner side of each air bag located adjacent thorax wall 113. Jackets 126 and 127 are made of rigid shells or non-elastic material that has sufficient rigidity to direct the pulsating forces, indicated by arrows 133 and 134, caused by changes of air pressure in air bags 128 and 129 to be directed inwardly into the body toward body cavity 114. Body 112 has reaction forces to the pressure pulses which further enhance the advantageous functions of device 100.

Air bags 128 and 129 are connected to a pulsator, indicated generally at 136, with air hoses 137 and 138. Hoses 137 and 138 carry pulses of air under pressure, indicated by arrows 139 and 141, to chambers 131 and 132 of air bags 128 and 129. Pulsator 136 is connected to air pump 142 with hose 143 and tubes 170 and 176. Air pump 142 operates to initially pressurize the air in pulsator 136, lines 137 and 138 and air bags 128 and 129. As seen in FIG. 4, line 143 is connected to check valve 144 operable to allow air into pulsator 136 and prevent the escape of air from pulsator 136 and air bags 128 and 129. Check valve 144 is connected to an air pressure distribution device, indicated generally at 168, operable to distribute the air pressure to opposite sides of pulsator 136.

Figure 5:
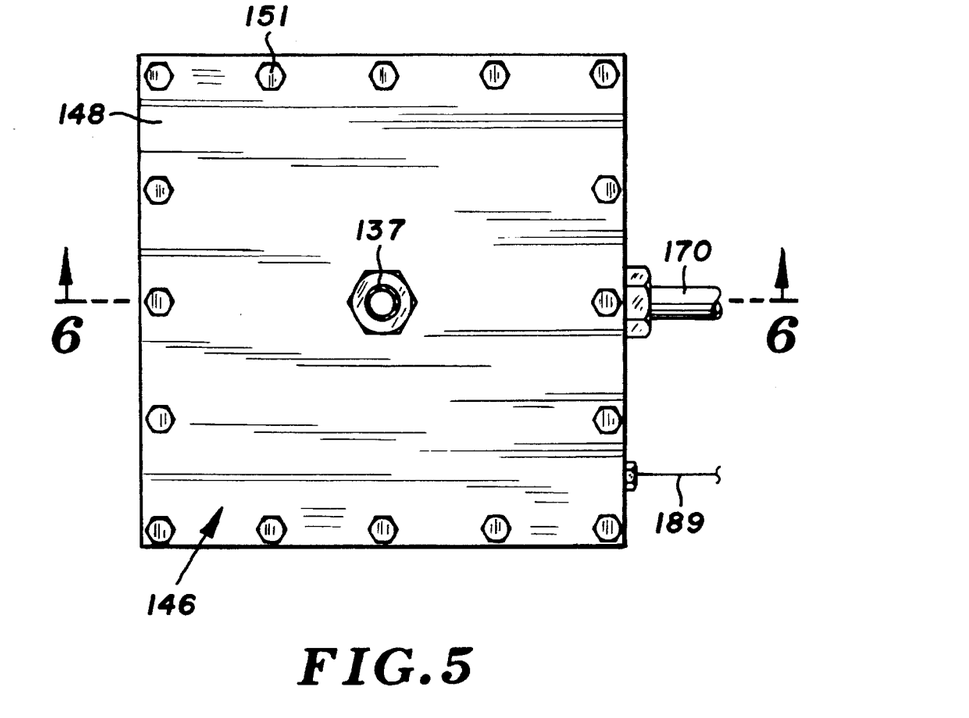
FIG. 5 is a top plan view of the pulsator of the medical device of FIG. 4.
Figure 6:
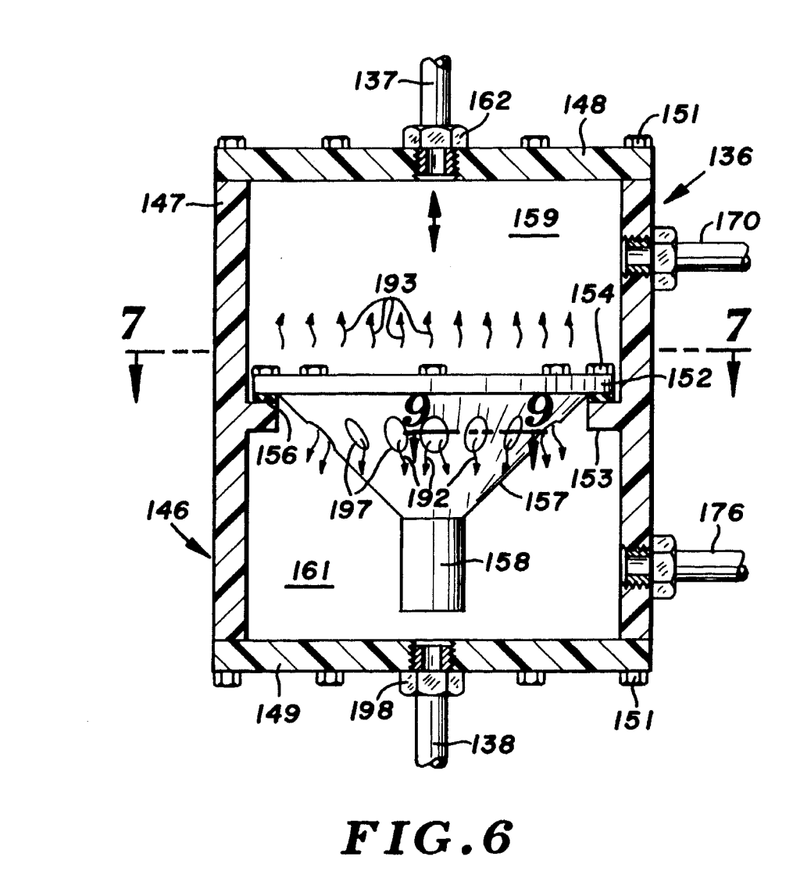
FIG. 6 is a sectional view taken along the line 6—6 of FIG. 5.
Figure 7:
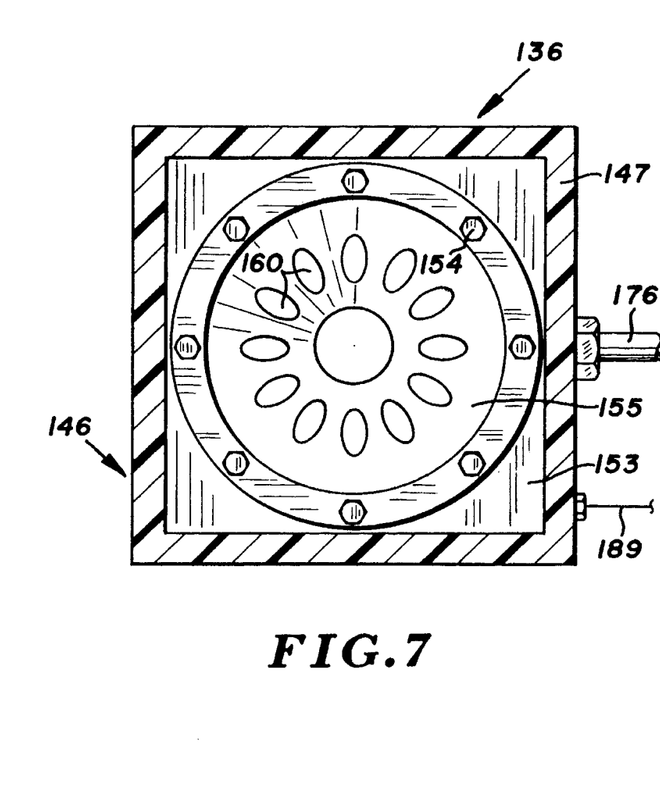
FIG. 7 is a sectional view taken along the line 7—7 of FIG. 6.
Figure 9:
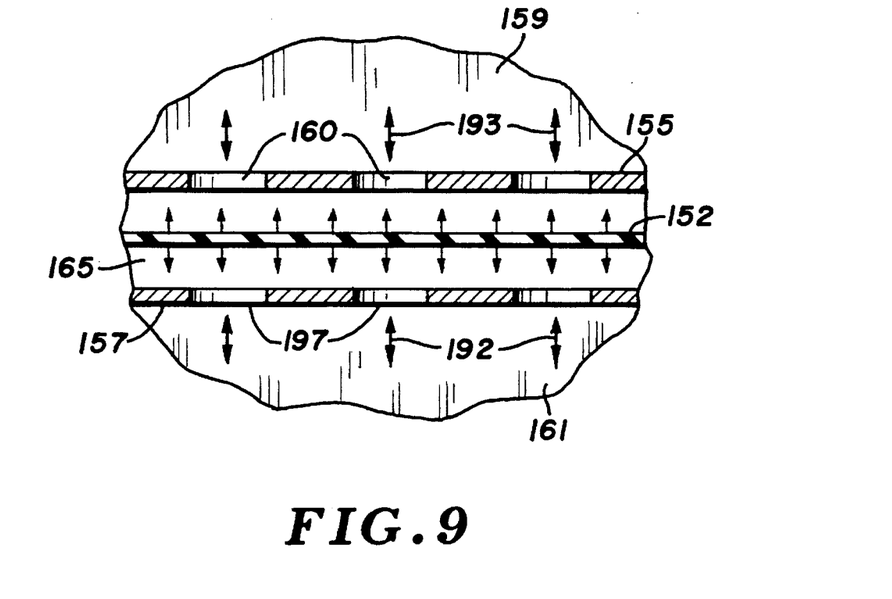
FIG. 9 is an enlarged sectional view taken along the line 9—9 of FIG. 6.

Pulsator 136, as seen in FIGS. 5, 6 and 7 has housing 146 comprising side wall 147 connected to end walls 148 and 149 with bolts 151. A cone-shaped diaphragm 152 bisects the midportion of housing 146. The outer edge portion of diaphragm 152 is mounted on an inwardly directed rib 153 with a plurality of bolts 154. Cushion or vibration insulation material 156 is interposed between diaphragm 152 and rib 153. Diaphragm 152 is located between conical shells 155 and 157 supporting an electric coil 158 operable to vibrate diaphragm 152. Shell 155 has a plurality of openings 160 circumferentially spaced from each other providing passages between first chamber 159 and the space 165 between shells 155 and 157. Air is free to flow through openings 160 so that when diaphragm 152 is vibrated, the air pressure differences cause air force pulses in line 137 and air bag 129. Shell 157 has a plurality of openings 197 located between diaphragm 152 and coil 158. Openings 197 are circumferentially spaced from each other and provide air passages between space 165 and second chamber 161. Air is free to flow through openings 197, as shown by arrows 192 in FIG. 6, between space 165 and chamber 161 so that when diaphragm 152 is vibrated, the air pressure differences cause air force pulses in line 138 and air bag 128. Diaphragm 152 bisects the internal space of housing 146 into first chamber 159 and second chamber 161. Openings 160 and 197 allow diaphragm 152 to generate air pressure differences or force pulses, indicated by arrows 192 and 193 in FIG. 9, in the air in second chamber 161 when diaphragm 152 is vibrated by action of coil 158. Diaphragm 151 is a flexible sheet member of plastic or rubber-like material located in spaced 165 midway between shells 155 and 157. In the event that the air pressure in either chamber 159 and 161 is released, diaphragm 151 will only flex until it engages the inside of one of the shells. This prevents rupture and air leakage of the diaphragm.

As shown in FIG. 6, hose 137 is secured to end wall 148 with tubular connector 162, which allows the air in chamber 159 to flow through hose 137 to air chamber 132 of air bag 129. A second hose 138 is connected to end wall 149 with a tubular connector 198 that carries air under pressure to chamber 131 of air bag 128 from chamber 161 of pulsator 136.

Returning to FIG. 8, check valve 144 has a connector or housing 163 having chamber 166 accommodating check ball 164. The inner end of chamber 166 is closed with perforated plug 167 to allow air to flow through check valve 144 into air pressure distribution device 168. Ball 164, when lowered on its seat, blocks the reverse flow of air from device 168 back into hose 143 leading to pump 142.

Figure 8:
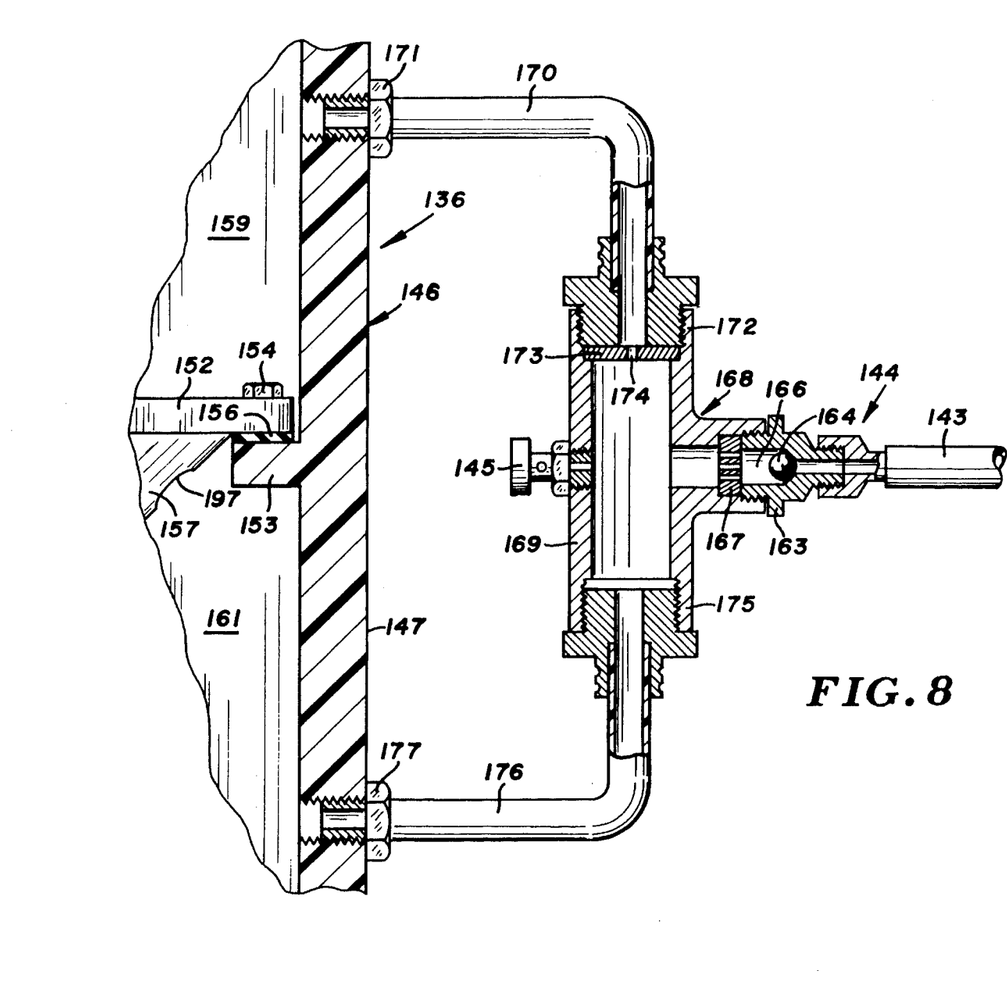
FIG. 8 is an enlarged sectional view of the check valve, pressure relief valve and the air-restricting washer connected to the air pump and the opposite chambers of the pulsator of the medical device shown in FIG. 4.

Air pressure distribution device 168 has a T-shaped member or coupling 169 having opposite ends 172 and 175 connected to a first elbow or tube 170 and a second elbow or tube 176, respectively. The inner end of check valve housing 163 is threaded into a third opening located on a middle portion of coupling 169. Tube 170 is connected to a nipple connector 171 mounted on side wall 147 and open to chamber 159. Tube 176 is connected to nipple connector 177 mounted on side wall 147 and open to chamber 161. Coupling end 172 accommodates a disk or member 173 having a small central hole 174 adjacent the outer end of hose 170 to restrict the flow of air between chambers 159 and 161. A manually-operated open and close valve 145 mounted on coupling 169 is used to vent air from chambers 159 and 161 and relieve the air pressure from air bags 128 and 129. Hoses 137 and 138 can also be uncoupled from end walls 148 and 149 to allow air to escape to the atmosphere.

Returning to FIG. 4, pulsator 136 is driven with wave generator 178 connected to an electrical power source with plug 179. Wave generator 178 has a plurality of switches 181, 182 and 183 operable to select a desired wave form, such as a square wave, a sinusoidal wave or a spike wave. Generator 178 has a wave frequency control 194 having an adjusting dial 196. Operator or patient 111 can manually use dial 196 to adjust the frequency of the signal sent to amplifier 186. The operator or patient 111 can select the wave form and frequency of the signal with generator 178. Amplifier 186 is used to control the power of the signal sent to coil 158 thereby controlling the vibrations and air pumping characteristics of diaphragm 152. Line 184 connects generator 178 to amplifier 186 which is powered by electrical power connected thereto with power plug 187. Amplifier 186 has a control 188 operable to adjust the amplification or gain of a power signal carried by line 189 to coil 158, thereby controlling the output power of coil 158 and amplitude of the vibrations of diaphragm 152. The vibrations of diaphragm 152 cause air pressure changes or flexion of pressure pulses which are alternately transmitted by the air in the system to air bags 128 and 129. The frequency of the power signal is determined by the operation of frequency control 194. Vibrating diaphragm 152 alternately generates air pressure differences or force pulses indicated by arrows 192 and 193 in FIGS. 5 and 9 in the air in chambers 159 and 161. These pulses are ripple pressure waves which increase and decrease the pressure of the air in chambers 159 and 161 and air bags 128 and 129 in air pressure change ranges of 0.25 psi at unsynchronized intervals. Other differences in air pressure can be alternately generated by pulsator 136.

In use, vest 124 is placed about body 112 of person 111 to cover the torso adjacent thoracic wall 113. Air pump 142 is operated to inflate air bags 128 and 129 to a selected pressure, such as 1 psi. Air pressure relief valves 130A and 130B are usable to prevent excessive air pressure in air bags 128 and 129. When the selected pressure is obtained, air pump 142 is turned OFF as check valve 144 maintains the air pressure in air bags 128 and 129, as well as pulsator 136. Wave generator 178 establishes the wave form and frequency which is amplified by amplifier 186 to drive coil 158. Operation of coil 158 causes diaphragm 152 to vibrate thereby establishing the alternating ripple pressure waves in chambers 159 and 161 of pulsator 136. The result is that air bags 128 and 129 alternately transmit controlled air pressure pulses, as indicated by arrows 133 and 134 in FIG. 4, to the front and back of thoracic wall 113 to facilitate the loosening and elimination of mucus from the lungs of person 111, aid blood circulation and relieve muscular and nerve tensions. To remove vest 124 from body 112, valve 145 is opened to vent air from the system thereby deflating air bags 128 and 129.

While there have been shown and described several embodiments of the device of the invention and uses thereof, it is understood that changes in structures, components and arrangement of structures can be made by one skilled in the art without departing from the invention. The invention is defined in the following claims.

I claim:

1. An apparatus for generating repetitive air pressure pulses for a first receiver and a second receiver comprising: housing means having an enclosed internal chamber, diaphragm means located within said chamber dividing the chamber into a first chamber means and a second chamber means, means for supplying air under pressure to said first and second chamber means, coil means for vibrating the diaphragm means to pulsate the air in the first and second chamber means at different intervals, first means having a passage open to the first chamber means for carrying air under pressure to a first receiver whereby the first receiver is subjected to air pressure pulses, second means having a passage open to the second chamber means for carrying air under pressure to a second receiver whereby the second receiver is subjected to air pressure pulses at different intervals from the air pressure pulses applied to the first receiver, wave generator means for generating a wave signal, and means connecting the wave generator means to the coil means whereby the signal from the wave generator means energizes the coil means which vibrates the diaphragm means to pulsate the air alternately in said first chamber and second chamber.

2. The apparatus of claim 1 including: amplifier means connected to the wave generator means for amplifying the wave signal to control the output power of the coil means thereby controlling the vibration intensity of the diaphragm means.

3. The apparatus of claim 2 wherein: said amplifier means includes control means to adjust the gain of the output signal of the amplifier means thereby adjusting the output power of the coil means.

4. The apparatus of claim 1 wherein: the wave generator means includes means to adjust the frequency of the wave signal generated by the wave generator means.

5. The apparatus of claim 1 wherein: the wave generator means includes means to change the wave form of the wave signal generated by the wave generator means.

6. The apparatus of claim 1 wherein: the wave generator means includes first means to change the wave form of the wave signal generated by the wave generator means, and second means to adjust the frequency of the wave signal generated by the wave generator means.

7. The apparatus of claim 1 wherein: the means for supplying air under pressure to said first and second chambers includes tubular means having an air passage connecting said first and second chambers, and means having a hole located in said air passage to restrict the flow of air between said first and second chambers.

8. The apparatus of claim 1 including: means mounting the diaphragm means on said housing means to locate the diaphragm means within said internal chamber.

9. The apparatus of claim 1 including: shell means located within the second chamber connecting the diaphragm means with the coil means, and means mounting the shell means on said housing means to locate the diaphragm means, shell means and coil means within said internal chamber.

10. The apparatus of claim 9 wherein: the shell means includes spaced shells, said diaphragm means being located between said shells, each of said shells having at least one opening allowing the diaphragm means to pulsate air in the first and second chamber means when the diaphragm means is vibrated.

11. The apparatus of claim 1 including: check valve means connected to the means for supplying air under pressure to said first and second chamber means for preventing escape of air from said chamber means.

12. An apparatus for providing repetitive pressure pulses to first and second portions of a person comprising: means having first and second flexible air-accommodating means engageable with the first and second portions of a person that are to be subjected to repetitive pressure pulses, a pulsator operable to produce first and second air pressure pulses, first hose means connecting the pulsator with the first air-accommodating means whereby the first air pressure pulses provided by the pulsator repetitively move the first air-accommodating means which applies first pressure pulses to said first portion of a person, second hose means connecting the pulsator with the second air-accommodating means whereby the second air pressure pulses provided by the pulsator repetitively move the second air-accommodating means unsynchronized with the repetitive movement of the first air-accommodating means thereby applying second pressure pulses to said second portion of a person at different intervals from the application of the first pressure pulses to the first portion of a person, said pulsator having housing means including an enclosed chamber, diaphragm means located within said chamber dividing the chamber into a first chamber means and a second chamber means, means for supplying air under pressure to the first and second chamber means, coil means for vibrating the diaphragm means to pulsate air in the first and second chamber means at different intervals, said first hose means being connected to the housing means and open to the first chamber means whereby air in said first air-accommodating means is pulsated, which in turn subjects the first portion of a person to the first pressure pulses, said second hose means being connected to the housing and open to the second chamber means whereby air in the second air-accommodating means is pulsated in opposite rhythmic pattern from pulsation of air in the first air-accommodating means, subjecting the second portion of a person to the second pressure pulses at different intervals from the first pressure pulses applied to the first portion of a person, wave generator means for generating a wave signal, and means connecting the wave generator means to the coil means whereby the signal from the wave generator means energizes the coil means, which vibrates the diaphragm means to pulsate air alternately in said first and second chamber means.

13. The apparatus of claim 12 including: amplifier means connected to the wave generator means for amplifying the wave signal to control the output power of the coil means thereby controlling the vibration intensity of the diaphragm means and the force of the first and second pressure pulses applied to the person.

14. The apparatus of claim 13 wherein: said amplifier means includes control means to adjust the gain of the output signal of the amplifier means thereby adjusting the output power of the coil means.

15. The apparatus of claim 12 wherein: the wave generator means includes means to adjust the frequency of the wave signal generated by the wave generator means.

16. The apparatus of claim 12 wherein: the wave generator means includes means to change the wave form of the wave signal generated by the wave generator means.

17. The apparatus of claim 12 wherein: the wave generator means includes first means to change the wave form of the wave signal generated by the wave generator means, and second means to adjust the frequency of the wave signal generated by the wave generator means.

18. The apparatus of claim 12 wherein: the means for supplying air under pressure to said first and second chamber means includes tubular means having an air passage connecting said first and second chamber means, and means having a hole located in said air passage to restrict the flow of air between said first and second chambers.

19. The apparatus of claim 12 including: means mounting the diaphragm means on said housing means to locate the diaphragm means within said internal chamber.

20. The apparatus of claim 12 including: shell means located within the second chamber connecting the diaphragm means with the coil means, and means mounting the shell means on said housing means to locate the diaphragm means, shell means and coil means within said internal chamber.

21. The apparatus of claim 20 wherein: the shell means includes spaced shells, said diaphragm means being located between said shells, each of said shells having a plurality of openings, allowing the diaphragm means to pulsate air in the first and second chamber means when the diaphragm means is vibrated.

22. The apparatus of claim 12 including: check valve means connected to the means for supplying air under pressure to said first and second chamber means for preventing escape of air from said chamber means.

23. An apparatus for providing repetitive pressure pulses to first and second portions of a person comprising: means having first flexible air-accommodating means engageable with the first portion of a person that is to be subjected to repetitive pressure pulses and second flexible air-accommodating means engageable with the second portion of a person that is to be subjected to repetitive pressure pulses, a pulsator operable to produce first and second air pressure pulses, first means having an air passage connecting the pulsator with the first air-accommodating means whereby the first air pressure pulses provided by the pulsator repetitively move the first air-accommodating means which applies pressure pulses to the first portion of a person, second means having an air passage connecting the pulsator with the second air-accommodating means whereby the second air pressure pulses produced by the pulsator move the second air-accommodating means unsynchronized with the repetitive movement of the first air-accommodating means which applies pressure pulses to the second portion of a person at different intervals from the application of pressure pulses to the first portion of a person, said pulsator having housing means including an internal chamber, diaphragm means located within said internal chamber dividing the internal chamber into a first chamber and a second chamber, means for supplying air under pressure to the chambers, means for vibrating the diaphragm means to pulsate air in the chambers at different intervals, the air passage of the first means being connected to the housing means and open to the first chamber whereby air in said first air-accommodating means is pulsated, which in turn subjects the first portion of a person to repetitive pressure pulses, the air passage of the second means being connected to the housing means and open to the second chamber whereby air in said second air-accommodating means is pulsated opposite from the pulsation of air in the first air-accommodating means subjecting the second portion of a person to repetitive pressure pulses at different intervals from the pressure pulses applied to the first portion of a person, wave generator means for generating a wave signal, and means connecting the wave generator means to the means for vibrating the diaphragm means whereby the wave signal from the wave generator means energizes the means for vibrating the diaphragm means to pulsate air alternately in said first and second chambers and first and second air-accommodating means.

24. The apparatus of claim 23 including: amplifier means connected to the wave generator means for amplifying the wave signal to control the output of the means for vibrating the diaphragm means thereby controlling the vibration intensity of the diaphragm means and the force of the pressure pulses applied to the person.

25. The apparatus of claim 24 wherein: said amplifier means includes control means to adjust the gain of the output signal of the amplifier means thereby adjusting the output power of the means for vibrating the diaphragm means.

26. The apparatus of claim 23 wherein: the wave generator means includes means to adjust the frequency of the wave signal generated by the wave generator means.

27. The apparatus of claim 23 wherein: the wave generator means includes means to change the wave form of the wave signal generated by the wave generator means.

28. The apparatus of claim 23 wherein: the wave generator means includes first means to change the wave form of the wave signal generated by the wave generator means, and second means to adjust the frequency of the wave signal generated by the wave generator means.

29. The apparatus of claim 23 including: means mounting the diaphragm means on said housing means to locate the diaphragm means within said internal chamber.

30. The apparatus of claim 23 including: shell means located within the second chamber connecting the diaphragm means with the coil means, and means mounting the shell means on said housing means to locate the diaphragm means, shell means and coil means within said internal chamber.

31. The apparatus of claim 30 wherein: the shell means includes spaced shells, said diaphragm means being located between said shells, each of said shells having a plurality of openings, allowing the diaphragm means to pulsate air in the first and second chambers when the diaphragm means is vibrated.

32. The apparatus of claim 23 including: check valve means connected to the means for supplying air under pressure to said first and second chambers for preventing escape of air from said chambers.

* * * * *